US005585234A

United States Patent [19]

Naz et al.

[11] Patent Number: 5,585,234
[45] Date of Patent: Dec. 17, 1996

[54] TREATMENT OF INFERTILE SPERM IN VITRO WITH THYMOSIN $\alpha_1$ TO ENHANCE PENETRATION OF MAMMALIAN OVA

[75] Inventors: Rajesh K. Naz, Bronx, N.Y.; Allan L. Goldstein, Bethesda, Md.

[73] Assignees: The George Washington University Medical Center, Washington, D.C.; Albert Einstein College of Medicine, Bronx, N.Y.

[21] Appl. No.: 227,990

[22] Filed: Apr. 15, 1994

Related U.S. Application Data

[63] Continuation of Ser. No. 977,851, Nov. 17, 1992, abandoned.

[51] Int. Cl.⁶ .............. A01N 1/02; A61D 19/00; A61K 38/16; C12N 5/06
[52] U.S. Cl. .............. 435/2; 435/240.2; 530/324; 530/399; 600/33
[58] Field of Search .............. 435/2, 240.2; 514/2, 514/12; 530/301, 324, 399; 600/33; 604/35, 906

[56] References Cited

U.S. PATENT DOCUMENTS 4,444,757  4/1984  Strausser .................. 514/21
4,950,590  8/1990  Mutchnick et al. .................. 435/7.92

FOREIGN PATENT DOCUMENTS 0056594  7/1982  European Pat. Off. .

OTHER PUBLICATIONS

Naz et al., Biol. of Reprod., 47:1064–72, 1992.
Milton G. Mutchnick, et al., "Thymosin Treatment Of Chronic Hepatitis B: A Placebo–Controlled Pilot Trial", *Hepatology* vol. 14, No. 3, 1991, 409–415.
Harris et al., TIBTECH, vol. 11, pp. 42–44, 1993.
Foon, Cancer Res., vol. 49, pp. 1621–1639, 1989.
Seibel, New England J. Med., vol. 318, No. 13, 1988 pp. 828–834.
Waldmann, Science, vol. 252, 21 Jun., 1991 pp. 1657–1662.
Naz et al., Int J. Fertil., vol. 32, No. 5, 1987 pp. 375–379.

*Primary Examiner*—Ronald B. Schwadron
*Attorney, Agent, or Firm*—Rothwell, Figg, Ernst & Kurz

[57] ABSTRACT

The present invention relates to a method for increasing penetration of mammalian ova by mammalian male sperm by contacting sperm in vitro with a penetration-enhancing amount of a penetration-enhancing thymosin polypeptide or a penetration enhancing anti-thymosin antibody. In preferred embodiments, treatment comprises contacting mammalian sperm with thymosin $\alpha_1$ or antibodies to thymosin $\alpha_1$ or thymosin $\beta_4$.

4 Claims, No Drawings

1

TREATMENT OF INFERTILE SPERM IN VITRO WITH THYMOSIN $\alpha_1$ TO ENHANCE PENETRATION OF MAMMALIAN OVA

STATEMENT OF GOVERNMENT INTEREST

This invention was made with Government support under NIH Grant No. HD 24425. As such, the Government has certain rights in this invention.

This is a continuation of application Ser. No. 07/977,851, filed Nov. 17, 1992, now abandoned.

FIELD OF INVENTION

This invention relates to methods for treating infertility in mammalian males. More particularly, the invention relates to the use of certain thymosin polypeptides and antibodies to treat male infertility.

BACKGROUND OF THE INVENTION

The thymus is involved in immunologic and endocrinologic homeostasis of the body. See Besedovsky, et al. *Nature* 249:356–361 (1974). The importance of the thymus gland in the development and senescence of immunological competence in mammals now is generally accepted. Various factors of the thymus gland are recognized to modulate the levels of sex steroids which in turn can cause spontaneous and experimentally induced autoimmune diseases and alter the immune response during pregnancy. See Oates, et al., *Trends Pharmacol. Sci.* 5:347 (1984). Several humoral factors possessing hormone-like activity have been isolated and characterized from the thymus or its extracts. See e.g., Goldstein, et al. *Proc. Natl. Acad. Sci.* 74:725–729 (1977). Factors which have been isolated include prothymosin-α (ProTα), thymosin-$\alpha_1$ (T$\alpha_1$) and thymosin-$\beta_4$ (T$\beta_4$). T$\alpha_1$ and T$\beta_4$ have been sequenced and synthesized. The sequence of T$\alpha_1$ is shown, for example, in U.S. Pat. No. 4,079,127 (Goldstein et al.). The sequence of T$\beta_4$ is provided in U.S. Pat. No. 4,297,276 (Goldstein, et al.).

The presence of T$\alpha_1$ in human seminal plasma and in human follicular fluid has been reported. See Naz et al., *Int. J. Fertil.* 32:375 (1987), incorporated herein by reference. Naz et al. reported that there was a correlation between the amount of T$\alpha_1$ in the seminal plasma and sperm counts and semen volume and that levels were significantly lower in males with defective sperm function.

Fertilization is a complex process requiring the spermatozoa to undergo a cascade of events before fusing with the egg plasma membrane. This chain of events includes capacitation of the sperm binding to the zona pellucida, acrosome reaction, and penetration through the zona pellucida, all as described in Naz et al., *Current Opin. Immunol.* 2:748–751 (1990). Capacitation is a physiological process that a mammalian sperm cell must undergo before it can fertilize an oocyte.

Infertility remains a problem for a substantial portion of the population. Cumulative data indicate that as many as one in four married couples in the United States who wish to have children have difficulty in conceiving a child. A number of techniques, such as artificial insemination, micromanipulation of the gametes and in vitro fertilization, have been developed in recent years in efforts to overcome some of the causes of the problem. Many of these techniques are quite expensive, however, and the success rates have been low. Accordingly, there exists a substantial need for compositions and methods useful in the treatment of infertility.

SUMMARY OF THE INVENTION

It is an object of the present invention to provide compositions and methods for the treatment of infertility in mammalian males. More specifically, it is an object of the present invention to provide treatments for infertility in mammalian males caused by defective sperm function.

This and other objects are accomplished through the administration of a fertility-enhancing thymosin peptide, such as T$\alpha_1$, or a fertility enhancing anti-thymosin antibody, such as an anti-T$\alpha_1$ or anti-T$\beta_4$ antibody, in a fertility enhancing amount. The thymosin peptide or anti-thymosin antibody can be administered in vitro by collecting sperm from semen of an infertile male and incubating them with the fertility enhancing thymosin peptide or anti-thymosin antibody for a period of time sufficient to enhance the fertilizing capacity of the sperm. The sperm then are washed and incubated with ova under conditions whereby the egg can be fertilized.

Alternatively, the fertility enhancing thymosin can be administered in vivo in amounts sufficient to enhance the fertilizing capacity of the sperm.

DETAILED DESCRIPTION OF THE INVENTION

One embodiment of the present invention relates to the use of a fertility-enhancing thymosin peptide to treat infertile mammalian males. As used herein, a "fertility-enhancing thymosin peptide" means a thymosin peptide which enhances the ability of sperm to fertilize an egg. The ability of sperm to fertilize an egg can be improved, for example, by enhancing sperm capacitation or by enhancing acrosomal reaction by sperm and can be evidenced by an increase in the sperm that penetrate eggs. Such thymosin polypeptides include T$\alpha_1$ and biologically active analogs and fragments thereof. The thymosin polypeptide can be naturally isolated, recombinantly produced or synthetic.

Treatment with the thymosin molecule can be carried out either in vitro or in vivo. For in vitro treatment, the thymosin peptide is added to sperm collected from semen of an infertile mammalian male and incubated for a time period sufficient to increase the fertilizing capacity of the sperm, typically from about 5 to 10 hours. After incubation, the sperm sample can be washed and incubated with isolated ova. The incubation can be in vitro or in vivo according to known techniques.

Alternatively, the thymosin peptide also can be administered in vivo. In one embodiment, the thymosin can be administered to the infertile male in a series of injections sufficient to increase the amount of thymosin in his seminal plasma and the fertilizing capacity of his sperm. Alternatively, the thymosin can be administered to a mammalian female so as to provide the thymosin in the female's vaginal tract whereby it then can react with sperm entering the vaginal tract and increase the sperm's fertilizing capacity. For example, the thymosin peptide can be injected and the thymosin in the bloodstream can pass across membranes into the vaginal tract and thus be available to react with sperm. Alternatively, the thymosin can be formulated into a slow release capsule that is inserted into the female's vaginal tract. The capsule slowly releases the thymosin which then can react with sperm cells entering the vaginal tract to enhance the fertilizing capacity of the sperm.

A preferred fertility enhancing thymosin peptide for in vitro or in vivo administration comprises T$\alpha_1$ or biologically active analogs or fragments thereof. T$\alpha_1$ is known to those of skill in the art and is available, for example, from Alpha 1 Biomedicals, Inc. in Bethesda, Md. The structure of $T\alpha_1$ is disclosed in U.S. Pat. No. 4,079,127. As used herein, $T\alpha_1$ shall include a peptide having the structure of $T\alpha_1$ disclosed in U.S. Pat. No. 4,079,127 or bioactive analogs or fragments of that molecule, such as those disclosed in U.S. Pat. No. 4,612,365. Preferably, such fragments are from 4 to 18 amino acids in length, including salts thereof, which maintain thymosin activity.

In another embodiment of the present invention, as discussed below, fertility enhancing anti-thymosin antibodies are administered in vitro to treat infertility in mammalian males. As used herein, "fertility-enhancing anti-thymosin antibodies" means polyclonal or monoclonal antibodies to a thymosin peptide that increase the fertilizing capability of the sperm. The thymosin peptide can be natural, recombinant or synthetic and includes the full length peptide and biologically active analogs or fragments thereof. Fertility enhancing antibodies include anti-$T\alpha_1$ antibodies and anti-$T\beta_4$ antibodies.

As noted above, in one method of the present invention, sperm from semen from an infertile mammalian male are collected and treated with fertility enhancing thymosin peptides or fertility enhancing anti-thymosin antibodies prior to incubation with ova.

Methods for collecting semen are known to those of skill in the art and the invention is not directed to such methods. Preferably, the semen will be liquified and the swim-up sperm population collected. Preferably, the liquification will occur with heating for 15 to 30 minutes at 37° C. Such a procedure is described in Naz et al., *J. Cell Sci.*, 99:157–165 (1991). The collected sperm cells from the swim-up form a sperm suspension which is washed. Suitable media for the suspending and washing procedures include Biggers, Witten and Wittingham ("BWW") medium and Ham's F-10 medium (obtained from Gibco, N.Y.). It is preferable to supplement the medium with bovine serum albumin ("BSA"). A 1% supplementation is sufficient, although other supplementations can be used. The sperm concentration of the sample is adjusted as desired. Generally, suitable concentrations are within the range of from about 5 to about $10 \times 10^6$ motile sperm per milliliter of medium. The sperm then are incubated with the fertility-enhancing thymosin peptides. Preferably, the incubation is carried out at about 37° C. under a carbon dioxide enhanced atmosphere. A preferred atmosphere has been determined to comprise 95% air and 5% carbon dioxide. The incubation time can vary. Usually, however, an incubation time ranging from about 5 to about 10 hours, preferably from about 5 to 8 hours, is sufficient to allow capacitation to occur.

The amount of thymosin to be added to the sperm-containing sample also can vary. Effective concentrations can be determined by those of skill in the art having at their disposal the disclosure of the present invention. Typically, the concentration is within the range of about 0.05 to about 10 micrograms per 100 microliters of the sperm suspension. Preferably, the concentration of the thymosin is within the range of about 0.05 to about 0.5 micrograms per hundred microliters of the sperm suspension. Determination of a suitable amount can be made by persons of ordinary skill in the art based upon the amount of time needed for the sperm to capacitate. Desirably, sufficient thymosin is added to enable the sperm to capacitate within about 5 to 10 hours.

After the incubation period, the sperm are washed with medium again preferably supplemented with 1% BSA. At this juncture, the sperm are ready to be incubated with oocytes. The contact can be either in vitro by artificial insemination or in vivo. Thus, eggs can be isolated from females and fertilized with the treated sperm prior to reimplantation. Alternatively, the thymosin-treated sperm can be incubated with eggs in vivo. Techniques for application in both instances are known to those of skill in the art.

As an alternative to treating sperm cells with an effective amount of a fertility enhancing thymosin, the sperm cells can be treated with an effective amount of a fertility enhancing anti-thymosin antibody. Suitable antibodies include anti-thymosin antibodies that are effective in stimulating sperm penetration rates, such as by increasing sperm capacitation.

In preferred embodiments of this invention, the antibodies are selected from antibodies to $T\alpha_1$ and $T\beta_4$. Such antibodies can comprise polyclonal antisera or monoclonal antibodies. Monoclonal antibodies can comprise, for example, mouse or human monoclonal antibodies. In general, techniques for generating monoclonal antibodies are known. See, for example, Naz et al., *Science*, 225:342–344 (1984) and Naz et al., *PNAS USA*, 83:5713–5717 (1986). If polyclonal antibodies are used, they can comprise polyclonal antiserum from mammals such as rabbits, mice or rats. In order to obtain the preferred antiserum, $T\alpha_1$ or $T\beta_4$ can be coupled to a suitable carrier protein. Such carrier proteins are known to those of skill in the art and include, for example, keyhole limpet hemocyanin (KLH), diphtheria toxoid, tetanus toxoid, thyroglobulin, human serum albumin and so forth. The coupling is performed using techniques known to those of skill in the art. Known coupling agents can be used. A preferred coupling agent is glutaraldehyde.

Having obtained suitable immunogens, the animal of choice is immunized. Suitable immunization techniques are known to those of skill in the art. Typically, however, the rabbit or other animal is injected at intramuscular and subcutaneous sites with the immunogen emulsified in Freund's complete adjuvant. While booster schedules can vary, preferably boosters are administered on a weekly basis after two weeks. Boosters can continue for as long as required. Typically, it has been found that three weeks of boosters are sufficient, for example, when using rabbits. At various times during the immunization process, blood can be withdrawn from the animal and titered for the presence of desired antibody. Usually, one week after the last booster, the animals will be bled and the antisera titered. If desired, the antibodies then can be affinity purified using a Protein-A Sepharose column. There are various techniques for bleeding animals. As is known to those of skill in the art, booster administrations of the immunogen typically comprise the immunogen emulsified with Freund's incomplete adjuvant.

When antibodies are used in a method of the present invention, they are incubated with a sperm suspension as previously described for the incubation with the thymosin peptides. Typically, the antibody concentration can vary from about 5 to about 25 microliters of antiserum per 100 microliters of sperm suspension. As an exemplary illustration, not to be considered limiting, a preferred concentration range for both $T\alpha_1$ and $T\beta_4$ antisera is from about 10 to about 20 microliters of antiserum per 100 microliters of sperm suspension, or about 2 µg to about 10 µg of specific IgG per 100 µl.

At the conclusion of the incubation period, the sperm cells are washed. In this instance, the wash removes the unreacted antibody. Again, the washed sperm cells then can be incubated with eggs as discussed above.

In addition to the in vitro treatment of sperm cells with fertility enhancing thymosin peptides and antibodies, the thymosin peptides can be administered in vivo. In one example of this embodiment, a solution of the thymosin peptide is injected intravenously into the infertile mammalian male in one or more doses in amounts sufficient to enhance the fertilizing capacity of the sperm. The amount of polypeptide to be administered will depend upon a number of factors, including the level of $T\alpha_1$ in the patient's seminal plasma prior to treatment and sperm motility. The thymosin peptide is administered in an amount sufficient to enhance the fertilizing capacity of the male's sperm. This can be done by increasing the level of $T\alpha_1$ in the seminal plasma.

The thymosin also can be injected into a mammalian female prior to introduction of the infertile male's sperm into her vaginal tract. Thymosin injected into the blood stream can pass through membranes into the vaginal tract, where it then can react with sperm from the infertile male to increase the sperm's fertilizing capability.

For injection into males or females, a suitable pharmaceutical dosage unit of the thymosin peptide generally is within the range of about 900 to about 1200 µg/m² body surface area in a pharmaceutically acceptable carrier. Lyophilized preparations of the thymosin peptide which contain mannitol and phosphate buffer are dissolved in diluent prior to dispersing. It is convenient to dispense the thymosin in one ml. dose vials.

For a human, an administration regimen of twice weekly injections of about 1500 to about 1700 µg may be convenient. Dosages and length of treatment can be flexible and can be determined by the patient's clinical response to the thymosin.

Alternatively, as noted above, the thymosin peptide can be formulated into a biocompatible slow release capsule which is implanted in a mammalian female's vaginal tract. The capsule will slowly release the thymosin over time into the vagina where it can react with sperm from the infertile male to increase the sperm's fertilizing capacity. Methods of making biologically compatible, slow release capsules are well-known in the art. An example of a suitable capsule is described in Radomsky, et al., *Biol. of Reproduction*, 47:133–140 (1992). Typically, a capsule for implantation in a human female can have about 4 to about 6 mg. of the thymosin peptide.

Although not wishing to be bound by theory, it is believed that mammalian sperm cells treated with fertility-enhancing thymosin peptide or anti-thymosin antibody have enhanced capacitation and acrosome reaction which can provide the basis for their enhanced fertilization capacity. Sperm cells treated as previously described have been shown to release higher quantities of acrosin in the supernatant when compared to non-treated sperm cells. Thus, one embodiment of the invention comprises a process for increasing sperm capacitation, a physiological event during which sperm cells undergo various physiological and biochemical changes which enable them to penetrate egg cell membranes, which comprises contacting sperm with a capacitation-increasing amount of a fertility-enhancing thymosin peptide or anti-thymosin antibody. The amounts required for such effect have been described above.

In yet another embodiment, the present invention comprises a process for increasing the number of acrosome-reacted sperm by contacting the sperm with an acrosome reaction-inducing amount of a thymosin polypeptide or antibody. The acrosome is a very small body located at the anterior end of a spermatozoan, which must release its contents of acrosin if the sperm is to be capable of fertilizing an egg. The concentrations of thymosin necessary to effect this event have been described above.

The invention having been generally described, the following non-limiting examples are set forth as further illustrations of the invention.

EXAMPLE 1

Preparation of Polyclonal Antisera $T\alpha_1$ and $T\beta_4$ were covalently coupled to keyhole limpet hemocyanin (KLH) using equal amounts of antibody and KLH in the presence of glutaraldehyde. Young adult New Zealand rabbits were injected at intramuscular and subcutaneous sites with $T\alpha_1$-KLH or $T\beta_4$-KLH emulsified with Freund's complete adjuvant. After two weeks, the rabbits were immunized with the respective antigen preparations weekly for three weeks. The booster during these three weeks was emulsified with incomplete Freund's adjuvant. One week after the last injection, the animals were bled by retroorbital puncture and the antisera were titered using a radioimmunoassay.

To provide control antisera, the same procedure was followed except that rabbits were injected with the same amount of KLH without coupled thymosin peptides or with KLH conjugated to a control 30 amino acid long peptide designated HGP-30. This peptide is described in Achour, A., et al., *PNAS USA* 87:7045 (1990). All antisera were heat inactivated at a temperature of 56° C. for thirty minutes and stored at −20° C. until used.

EXAMPLE 2

Analysis of Antibody Binding with Human Sperm

The antibodies prepared in Example 1 were analyzed for their binding with methanol-fixed human sperm in an indirect, immunofluorescence technique (IFT) as described by Naz et al. *Proc. Acad. Sci.*, 81:857–861 (1984). Semen samples obtained from fertile men using the procedure described in Naz et al., *J. Cell Sci.* 99:157–165 (1991), were washed in PBS. A swim-up population of highly motile sperm was collected and again washed in PBS and then air-dried on a slide and fixed with methanol for 30 minutes at room temperature. Subsequently, the slide was air-dried and treated with the antisera at a 1:50 dilution with phosphate buffered saline (PBS) at room temperature for 1½ hours in a humid chamber. The antibody-binding was localized by incubating with fluorescein-labeled goat anti-rabbit antibodies (1:50 dilution), (Cappel Labs., Malvourne, Pa.). The slides were washed with PBS three times, mounted in 90% glycerol in PBS containing sodium azide (0.1%) and 1,4-diazibicyclo (2,2,2) octane (10 milligrams per milliliter) to reduce photobleaching during observation. Samples were kept at 4° C. in a humid chamber until examined.

The anti-$T\alpha_1$ antibody demonstrated binding predominantly with acrosomal regions of the methanol-fixed human sperm cells in the IFT. The anti-$T\beta_4$ antibody also reacted strongly with the acrosomal regions and reacted weakly with the tail regions of the methanol-fixed sperm cells. The absorption of these antibodies with $T\alpha_1$ or $T\beta_4$, respectively, (20 µl of antibody and 10 µg of $T\alpha_1$ or $T\beta_4$) significantly absorbed out the immunoreactivity of the antibodies with sperm cells. The normal rabbit serum or anti-KLH conjugate antibodies did not react with the methanol-fixed sperm cells.

EXAMPLE 3

Sperm Penetration Assay

Human sperm penetration assay of zona-free-hamster oocytes (SPA) was performed as described in Naz et al., *J. Cell Sci.*, 102:487–494 (1992). Superovulation was induced in adult female golden hamsters by intraperitoneal injections of 30 IU eCG (pregnant mare serum gonadotropin) (Sigma Chemical Co., St. Louis, Mo.) on day 1 of the cycle. After 55–72 hours, 20 IU hCG (human chorionic gonadotropin) (Sigma) were administered intraperitoneally. 15–17 hours later the animals were sacrificed and the mature unfertilized ova were collected from the oviducts. The ova were separated from the surrounding cumulus cells by incubation with 0.2% hyaluronidase in Biggers, Witten and Wittingham (BWW) medium and from the zonae pellucida by treatment with 0.1% pancreatic trypsin in BWW. The zona-free ova were twice washed in BWW and placed in the center of a tissue culture dish.

Semen from a fertile man was liquified for 15–30 minutes at 37° C. and the swim-up sperm population was collected. Collection techniques are described in Naz et al., *J. Cell Sci.*, 99:157–165 (1991). The sperm cells from the swim-up were washed with BWW supplemented with 1% BSA (Sigma Chemical Co.) adjusted to 5–10×10$^6$ motile sperm per milliliter and then allowed to incubate for 5–6 hours at 37° C. (in 5% $CO_2$ and 95% air mixture) with $T\alpha_1$ or $T\beta_4$ (0.1–10 micrograms per hundred microliters of the sperm suspension) or polyclonal antisera elicited in response to those immunogens (10–20 microliters of antiserum/100 microliters of sperm suspension) or the same amount of control antibodies (normal rabbit serum, anti-KLH antibodies or anti-HGP-30 antibodies) or the equivalent volume of PBS containing 0.5% BSA (PBS/BSA). After incubation the sperm were washed to remove the unreacted thymosin or anti-thymosin antibody and co-incubated with the zona-denuded hamster oocytes (30–50 eggs/treatment in each assay) for three to four hours. The oocytes were removed, thoroughly washed, fixed with 3% glyceraldehyde and stained with acetocarmine solution. Sperm penetration was determined by the presence of a swollen spermhead with a discernable tail in the cytoplasm of the ovum. Motility of sperm before and after incubation with ova was recorded. The assays were repeated at least three to eight times using different fertile donors and each sample tested with at least 82–480 oocytes.

The percentage of ova penetrated was calculated according to the following formula;

$$\% \text{ ova penetration} = \frac{\text{Total number of ova penetrated}}{\text{Total number of ova incubated}} \times 100$$

Using this assay it was determined that approximately 93–108% of ova were penetrated with sperm from fertile men, with an average of one sperm penetrated per oocyte. The results of the assay are shown in Table 1.

As can be seen from Table 1, $T\alpha_1$ significantly (P<0.001) increased (up to 2.6 fold) the percentage of ova penetrated compared to PBS-BSA-treated control sperm, tested at a concentration of 0.05 to 0.5 µg $T\alpha_1$/100 µl sperm suspension.

As shown in Table 2, antibodies to both $T\alpha_1$ and $T\beta_4$ significantly (P<0.001) increased (up to 4.7 fold) the penetration rates in a concentration dependent manner. Antibodies to KLH carrier, to HGP-30/KLH conjugate or normal rabbit serum tested at the same concentration (20 µl/100 µl) did not affect penetration rates as compared to the PBS/BSA treated control sperm. Immunoabsorption of the anti-$T\alpha_1$ and anti-$T\beta_4$ antibodies with the respective peptides caused a significant (P<0.001) reduction in the fertilization-enhancing activity of the antibody.

The SPA also was performed on infertile (n=18) and fertile men (n=5), as indicated in Table 3 by the method of Syms et al., *Fertil. Steril.* 43:766 (1985). In this assay, liquified semen was combined with an equal volume of prewarmed (37° C.) test yolk buffer (described, for example, in Naz et al., *J. Cell Sci.*, 99:157 (1991)) and allowed to capacitate for 24 hr at 4° C. The sperm then were washed, added to the zona-free hamster oocytes and the number of sperm penetrated per ovum was determined by the procedure described above. 100% of ova were penetrated with sperm from fertile men, with an average of 26.2–34.9 sperm penetrated per oocyte (Table 3). If the sperm function was abnormal, there was a decrease in number of sperm penetrated per oocyte, and also a decrease in the percent ova penetrated, if the sperm abnormality was severe. The $T\alpha$ levels were significantly (P=0.002) lower in the seminal plasma of the infertile men as compared to those of fertile men (mean±S.D., infertile men, 1321.89±516.63; fertile men 2962.20±1811.25). The levels of $T\alpha_1$ correlated significantly (R=0.566, P was <0.01) within the number of sperm per ovum by SPA (Table 3).

EXAMPLE 4

Assessment of Acrosome Reaction

The effect of thymosin peptides and their antibodies were investigated on the human sperm acrosome reaction. The effect on acrosome reaction was assessed by determining the acrosomal status of the sperm after incubation with the antibodies or peptides as well as by studying the acrosin distribution after the acrosome reaction.

A. Assessment of Acrosomal Status

Motile sperm were collected from fertile men by the swim up procedure as set forth in Naz et al., referenced above. Good quality sperm samples, i.e., (5×10$^6$ motile sperm per milliliter), greater than 75% motility, +3 to +4 forward progression on a scale of 0 to +5 were incubated with $T\alpha_1$ or $T\beta_4$ or anti-$T\alpha_1$ antibodies or anti-$T\beta_4$ antibodies. The controls were treated with the same amount of normal rabbit serum, anti-KLH antibodies, anti-HGP 30 antibodies or PBS-BSA as previously described. After incubation, the spermatozoa were centrifuged, washed in PBS and divided into two aliquots. One aliquot was induced to acrosome react with calcium ionophore (Calcium ionophore A23187 (Sigma)) and incubated with sperm suspension for one hour. The other aliquot was allowed to spontaneously acrosome react without treating with calcium ionophore. Calcium ionophore treatment was carried out to induce acrosome reaction of the capacitated sperm. The acrosomal status was assessed using the triple stain procedure described by Jager et al., *Arch. Androl.*, 12:53–58 (1984). The sperm were washed twice in PBS and then incubated at 37° C. for fifteen minutes with 2% Trypan blue (Sigma 1:1 v/v) in PBS. After incubation, the sperm were washed twice, fixed in three percent glutaraldehyde, 0.1M cacodylate buffer for sixty minutes and then twice washed again in PBS. A drop of this suspension was placed on a glass slide and allowed to air dry overnight. The dried slide was stained with 0.8% Bismark Brown (Sigma) in deionized water (pH 1.8 with 2N HCl), rinsed in deionized water and stained for 45 minutes at room temperature in 0.8% Rose Bengal (Sigma) in 0.1M cacodylate buffer at pH 6.0. The slides were again washed in deionized water, dehydrated in an alcohol series, cleared in xylene and mounted with permount and a coverslip. A total of 200–500 sperm per sample were evaluated and recorded as either alive or dead. The alive sperm were further evaluated as acrosome-intact or acrosome-non-intact (reacted) sperm. The experiments were repeated 3–5 times using sperm of at least three different fertile donors.

The $T\alpha_1$ when tested at a concentration of 0.5 micrograms/microliter (dose at which $T\alpha_1$ significantly increased the penetration rates) significantly enhanced capacitation and acrosome reaction of the human sperm cells (Table 4). On incubation with the $T\alpha_1$ for 5–6 hours the sample demonstrated significantly higher percentage of acrosome-reacted sperm compared to the sperm samples treated with PBS-BSA (Table 4). The sperm samples treated with $T\alpha_1$ showed a higher percentage of acrosome-reactive sperm whether they were tested for spontaneous acrosome reaction (without ionophore treatment) or investigated after ionophore-induced acrosome reaction. The effects were more predominant after the ionophore treatment. $T\beta_4$ did not exhibit a significant effect.

The antibodies to both $T\alpha_1$ and $T\beta_4$ caused a significant increase in the percentage of acrosome-reacted sperm (Table 4). Again, the effects were apparent whether checked for spontaneous acrosome reaction or investigated after ionophore-induced acrosome reaction of the antibody-treated sperm, although the effects were more predominant after the ionophore treatment. No significant effect on the percentage of acrosome-reacted sperm was observed by treatment with antibodies to KLH or antibodies to HGP-30 peptide/KLH conjugate as compared to the PBS-BSA control.

B. Assessment of Acrosin Distribution

After incubation with the thymosin peptides or the anti-thymosin antibodies or control antibodies or PBS-BSA and with or without treating with calcium ionophore A23187 for one hour as described above, the sperm cells were centrifuged and the acrosin activity determined in the supernatant and cells by the method of Kennedy et al., *J. Androl.*, 10:21–27 (1989). Ninety microliters of the supernatant or the pelleted sperm cells suspended in 90 microliters of PBS were mixed with one milliliter of the reaction mixture. The reaction mixture comprises one milligram per milliliter of N-benzoyl-dl-arginine-P-nitraniline (BAPNA) hydrochloride in 0.055M HEPES buffer, 0.055M NaCl, 10% v/v (dimethylsulfoxide), 0.1% v/v TRITON X-100 (t-Octylphenoxypolyethoxyethanol). The solution then was incubated for three hours at room temperature. The reaction was stopped by the addition of 100 microliters of 0.5M benzamidine and the absorbance measured at 405 nanometers using a Beckman spectrophotometer. Acrosin activity was expressed as $\mu IU/10^6$ spermatozoa. The daily variability of the assay was normalized using a cryopreserved partially-purified human acrosin extract. The preparation of such extracts is taught by Naz et al., *J. Cell Sci.*, 102:487–494 (1992).

Incubation with $T\alpha_1$ (0.5 micrograms/100 microliters), anti-$T\alpha_1$ antibody (20 microliters/100 microliters) or anti-$T\beta_4$ antibody (20 microliters/100 microliters) demonstrated a significantly higher quantity of acrosin concentration released in the supernatant and a lower quantity of acrosin concentration in the sperm cells compared to the PBS-BSA treated sperm (Table 4) (P=0.04 to less than 0.001). The effects were apparent whether investigated with or without the ionophore treatment, although the effects were more predominant after ionophore treatment. None of the control antibodies demonstrated any effect on the acrosin distribution of sperm cells. $T\beta_4$ exhibited no significant effect.

C. Sperm Motion Analysis

After incubation with thymosin peptides or their antibodies for 5 to 6 hours as described above, an aliquot (7 microliters) of the sperm suspension was placed into a Makler chamber (*Sefi Medical Instruments, Israel*) and the sperm motion characteristics measured using a computerized semen analyzer (Cell Soft Cryo Resources, N.Y.). The parameter settings were 30 frames analyzed at an image frequency of 30 Hz, 3 frames minimum sampling for motility, 15 frames minimum sampling for both velocity and amplitude of the lateral head movement ("ALH") measurements, 10 micrometers per second threshold velocity, minimum linearity of 2.5 for ALH measurements and a cell size range of 4–40 pixels with a magnification calibration of 0.688 micrometers per pixel.

No effect on the percentage of motile sperm cells in the sample was seen upon treatment with either $T\alpha_1$, $T\beta_4$ (0.5 micrograms per hundred microliters) or their respective antibodies (20 microliters per hundred microliters). However, $T\alpha_1$, antibodies to $T\alpha_1$ and antibodies to $T\beta_4$ significantly affected the velocity, ALH and beat frequency of sperm cells. Effects were more apparent on the increase in ALH and beat frequency. Neither $T\beta_4$ peptide nor the control antibodies affected any motility characteristics of the sperm cells compared to the PBS-BSA treated control (Table 5).

TABLE 1

EFFECTS OF THYMOSIN $\alpha_1$ AND THYMOSIN $\beta_4$ ON HUMAN SPERM PENETRATION RATES

| Treatment (μg/100 μl) | Ova Tested (No.) | Ova penetrated % (Mean ± S.D.) |
| --- | --- | --- |
| 1. Thymosin $\alpha_1$ | | |
| 0.01 | 41 | 120.3 ± 11.6 |
| 0.05 | 82 | 268.2 ± 26.4[a] |
| 0.1 | 124 | 251.0 ± 36.3[a] |
| 0.5 | 167 | 204.0 ± 13.9[a] |
| 2.0 | 82 | 100.5 ± 0.7 |
| 10.0 | 261 | 102.2 ± 18.9 |
| 2. Thymosin $\beta_4$ | | |
| 0.1 | 122 | 102.7 ± 6.5 |
| 0.5 | 128 | 99.7 ± 10.1 |
| 2.0 | 173 | 61.8 ± 27.9[b] |
| 10.0 | 179 | 31.5 ± 12.2[a] |
| 3. Control | | |
| PBS-BSA | 302 | 96.9 ± 7.2 |

[a]vs. control, P < .001; [b]vs. control, p = .009; others were insignificant vs. control.

TABLE 2

EFFECTS OF THYMOSIN ANTIBODIES ON HUMAN SPERM PENETRATION RATES

| Antibody (μl/100 μl) | Antibody absorbed with (μg antigen) | Ova tested (No.) | (Ova penetrated %) (Mean ± S.D.) |
|---|---|---|---|
| 1. Anti-T$\alpha_1$ | | | |
| 10 | — | 83 | 121.0 ± 5.7[a] |
| 20 | — | 164 | 376.5 ± 55.7[b] |
| 20 | 10 | 171 | 208.5 ± 59.5[b] |
| 2. Anti-T$\beta_4$ | | | |
| 20 | — | 166 | 457.8 ± 68.4 |
| 20 | 10 | 170 | 250.0 ± 33.1[b1] |
| 3. Anti-KLH alone | | | |
| 20 | — | 83 | 108.0 ± 2.8 |
| 4. Anti-HGP-30 | | | |
| 20 | — | 84 | 83.5 ± 9.19 |
| 5. Normal rabbit serum | | | |
| 20 | — | 80 | 109.5 ± 12.0 |
| 6. Control | | | |
| PBS-BSA | — | 480 | 98.0 ± 6.9 |

[a]vs. control, P = .004; [b]and [b1]vs. control, P < .001; [b]vs. [b1], P < .001; others were insignificant vs. control

TABLE 3

THYMOSIN$\alpha_1$ AND THYMOSIN$\beta_4$ LEVELS IN SEMINAL PLASMA OF INFERTILE AND FERTILE MEN

| | Semen Analysis | | | Penetration Rates | | | |
| | | | | Sperm | | | |
| Patient (%) | Total sperm (×10$^6$) | Motility (%) | Normal sperm (%) | penetrated/ ovum (No.) | Ova penetrated (%) | T$\alpha_1$ Level (pg/ml) | T$\beta_4$ Level (pg/ml) |
|---|---|---|---|---|---|---|---|
| | | | | 1. Infertile Men | | | |
| 1. | 476 | 70 | 70 | 5.9 | 100 | 1115 | 381 |
| 2. | 165 | 82 | 76 | 24.1 | 100 | 1370 | — |
| 3. | 216 | 64 | 61 | — | — | 1222 | 352 |
| 4. | 41 | 68 | 56 | — | — | 1271 | 156 |
| 5. | 246 | 69 | 53 | 7.1 | 100 | 1403 | 369 |
| 6. | 19 | 62 | 69 | 18.1 | 100 | 1169 | 282 |
| 7. | 128 | 60 | 58 | 14.6 | 100 | 2171 | 318 |
| 8. | 73 | 61 | 77 | 14.2 | 100 | 1435 | 178 |
| 9. | 43 | 60 | 59 | 13.4 | 100 | 1007 | 2643 |
| 10. | 140 | 55 | 65 | 18.8 | 100 | 1330 | 805 |
| 11. | 81 | 47 | 53 | 22.3 | 100 | 2965 | 452 |
| 12. | 295 | 60 | 70 | — | — | 1436 | 294 |
| 13. | 46 | 32 | 24 | 6.5 | 40 | 616 | — |
| 14. | 230 | 50 | 64 | 22.14 | 100 | 1206 | — |
| 15. | 245 | 79 | 61 | 21.55 | 100 | 1123 | — |
| 16. | 28 | 21 | 19 | 3.2 | 62 | 942 | — |
| 17. | 41 | 18 | 27 | 0.55 | 42 | 938 | — |
| 18. | 241 | 59 | 56 | 17.2 | 100 | 1075 | 103 |
| | | | | 2. Fertile Men | | | |
| 1. | 632 | 82 | 84 | 34.9 | 100 | 1438 | 102 |
| 2. | 385 | 65 | 72 | 26.2 | 100 | 2175 | 197 |
| 3. | 1430 | 65 | 74 | 32.1 | 100 | 1931 | 354 |
| 4. | 383 | 76 | 83 | 29.7 | 100 | 5962 | 188 |
| 5. | 1336 | 68 | 76 | 31.3 | 100 | 3305 | 254 |

TABLE 3-continued

THYMOSINα₁ AND THYMOSINβ₄ LEVELS IN SEMINAL PLASMA OF INFERTILE AND FERTILE MEN

| Patient | Semen Analysis | | | Penetration Rates | | $T\alpha_1$ Level (pg/ml) | $T\beta_4$ Level (pg/ml) |
|---|---|---|---|---|---|---|---|
| (%) | Total sperm (×10⁶) | Motility (%) | Normal sperm (%) | Sperm penetrated/ ovum (No.) | Ova penetrated (%) | | |
| 3. Sperm Extract | | | | | | | |
| 1. LIS-perm extract (6.94 mg/ml) | — | — | — | — | | 1626 | 66 |

TABLE 4

EFFECTS OF THYMOSINS AND THEIR ANTIBODIES ON ACROSOME REACTION OF HUMAN SPERM[a]

| | Without Ionophore Treatment | | | With Ionophore Treatment | | |
|---|---|---|---|---|---|---|
| | Acrosomereacted | Acrosin Activity[b] | | Acrosomereacted | Acrosin activity[b] | |
| Treatment | sperm (%) (Mean ± SD) | Cells (Mean ± SD) | Supernatant (Mean ± SD) | sperm (%) (Mean ± SD) | Cells (Mean ± SD) | Supernatant (Mean ± SD) |
| 1. THYMOSINS (0.5 μg/100 μl) | | | | | | |
| $T\alpha_1$ | 18.5 ± 3.5[c] | 64.5 ± 6.4[c] | 27.5 ± 13.4[c] | 69.2 ± 3.6[c] | 30.6 ± 7.2[c] | 68.2 ± 16.6[c] |
| $T\beta_4$ | 14.5 ± 2.1 | 76.5 ± 9.1 | 21.0 ± 14.4 | 61.5 ± 4.8 | 38.5 ± 7.1 | 52.8 ± 16.2 |
| 2. ANTIBODIES (20 μl/100 μl) | | | | | | |
| Anti-$T\alpha_1$ | 16.4 ± 3.2[c] | 69.6 ± 11.0[c] | 26.3 ± 13.6[c] | 67.3 ± 4.2[c] | 31.0 ± 2.6[c] | 70.0 ± 6.5[c] |
| Anti-$T\beta_4$ | 17.0 ± 2.6[c] | 66.3 ± 8.5[c] | 25.0 ± 13.1[c] | 68.0 ± 3.5[c] | 32.6 ± 3.8[c] | 67.3 ± 8.0[c] |
| Anti-KLH alone | 12.7 ± 1.2 | 74.5 ± 7.8 | 19.0 ± 15.5 | 60.7 ± 4.03 | 41.2 ± 13.6 | 56.4 ± 8.9 |
| Anti-HGP-30 | 13.0 ± 1.4 | 73.0 ± 11.3 | 19.5 ± 13.4 | 61.5 ± 3.5 | — | — |
| 3. CONTROL | | | | | | |
| PBS-BSA | 12.6 ± 2.5 | 77.4 ± 10.0 | 15.0 ± 12.1 | 59.5 ± 3.9 | 43.2 ± 7.5 | 53.8 ± 10.4 |

[a]Assays (3–5) were performed on various days using sperm collected from at least three different fertile men.
[b]Acrosin activity was expressed as μ IU of acrosin/10⁶ sperm cells.
[c]vs. control, $P = .04$ to $< .001$; others were insignificant vs. control.

TABLE 5

EFFECTS OF THYMOSINS AND THEIR ANTIBODIES ON HUMAN SPERM MOTILITY PARAMETERS[a]

| | Percent | Motility characteristics (Mean ± S.D.) | | | |
|---|---|---|---|---|---|
| Treatment | Motility | Velocity | Linearity | ALH[b] | Beat Frequency |
| 1. THYMOSINS (0.5 μg/100 μl) | | | | | |
| $T\alpha_1$ | 80.3 ± 6.2 | 61.1 ± 3.0[c] | 3.9 ± 0.6 | 4.0 ± 0.3[c] | 13.7 ± 0.6[c] |
| $T\beta_4$ | 76.0 ± 4.3 | 58.5 ± 2.6 | 4.0 ± 0.6 | 3.7 ± 0.4 | 13.1 ± 0.3 |
| 2. ANTIBODIES (20 μl/100 μl) | | | | | |
| Anti-$T\alpha_1$ | 75.0 ± 5.0 | 60.9 ± 1.1[c] | 3.9 ± 0.7 | 3.8 ± 0.1[c] | 14.0 ± 0.2[c] |
| Anti-$T\beta_4$ | 75.0 ± 4.6 | 60.8 ± 1.8[c] | 4.0 ± 0.7 | 3.7 ± 0.2[c] | 13.3 ± 0.9[c] |
| Anti-KLH alone | 71.0 ± 7.5 | 56.8 ± 1.7 | 3.9 ± 0.2 | 3.6 ± 0.3 | 12.8 ± 0.3 |
| Anti-HGP-30 | 71.1 ± 5.6 | 57.1 ± 2.0 | 3.8 ± 0.3 | 3.7 ± 0.3 | 12.7 ± 0.3 |

TABLE 5-continued

EFFECTS OF THYMOSINS AND THEIR ANTIBODIES ON HUMAN SPERM MOTILITY PARAMETERS[a]

| Treatment | Percent Motility | Motility characteristics (Mean ± S.D.) | | | |
|---|---|---|---|---|---|
| | | Velocity | Linearity | ALH[b] | Beat Frequency |
| 3. CONTROL | | | | | |
| PBS-BSA | 78.0 ± 9.1 | 57.2 ± 2.7 | 3.8 ± 0.4 | 3.5 ± 0.4 | 12.6 ± 0.5 |

[a]Assays (n = 3–5) were performed on various days using sperm collected from at least three different fertile donors.
[b]ALH means amplitude of lateral head displacement.
[c]vs. control, P = .02 to < .001; others were insignificant vs. control.

What is claimed is:

1. A method for increasing penetration of mammalian ova by mammalian male sperm which comprises contacting sperm of an infertile mammalian male in vitro with a penetration-enhancing amount of thymosin $\alpha_1$.

2. The method of claim 1, which comprises:
   (a) collecting sperm from semen of an infertile mammalian male; and
   (b) incubating said sperm in vitro with a penetration-enhancing amount of thymosin $\alpha_1$ for a time period sufficient to enhance penetration of ova by said sperm.

3. The method of claim 2, wherein the sperm are collected in a suspension at a concentration of about $5–10 \times 10^6$ motile sperm per ml and the concentration of the thymosin $\alpha_1$ is within the range of about 0.05 to about 10 μg/100 μl of sperm suspension.

4. The method of claim 2, which further comprises incubating said sperm with ova.

* * * * *